United States Patent
Mui et al.

(10) Patent No.: US 6,537,530 B2
(45) Date of Patent: Mar. 25, 2003

(54) PHTHALATE FREE NAIL POLISH ENAMEL COMPOSITION EMPLOYING NOVEL PLASTICIZERS

(75) Inventors: Ronnie F. Mui, Reading, PA (US); Thomas R. Candia, Cedar Grove, NJ (US); George H. Armstrong, Dayton, NJ (US); Michelle E. Pepe, South Plainfield, NJ (US)

(73) Assignee: Tevco, Inc., South Plainfield, NJ (US)

( * ) Notice: Subject to any disclaimer, the term of this patent is extended or adjusted under 35 U.S.C. 154(b) by 0 days.

(21) Appl. No.: 09/918,141

(22) Filed: Jul. 30, 2001

(65) Prior Publication Data

US 2002/0176830 A1 Nov. 28, 2002

Related U.S. Application Data

(60) Provisional application No. 60/264,400, filed on Jan. 26, 2001.

(51) Int. Cl.$^7$ .................. A61K 7/04; A61K 7/043
(52) U.S. Cl. ............................................... 424/61
(58) Field of Search ..................... 424/61, 59

(56) References Cited

U.S. PATENT DOCUMENTS

| | | |
|---|---|---|
| 4,097,589 A | 6/1978 | Shansky |
| 4,222,908 A | 9/1980 | Ikeda et al. |
| 4,649,045 A | 3/1987 | Gaske et al. |
| 5,093,108 A | 3/1992 | Pappas et al. |
| 5,133,966 A | 7/1992 | Khamis |
| 5,174,996 A | 12/1992 | Weber et al. |
| 5,180,847 A | 1/1993 | Thurman et al. |
| 5,210,066 A | 5/1993 | Sakurai et al. |
| 5,277,899 A | 1/1994 | McCall |
| 5,284,885 A * | 2/1994 | Nehra .................. 424/61 |
| 5,290,543 A | 3/1994 | Ounanian et al. |
| 5,523,076 A | 6/1996 | Schoon |
| 5,599,530 A | 2/1997 | Patil et al. |
| 5,601,808 A | 2/1997 | Mellul et al. |
| 5,607,665 A | 3/1997 | Calello et al. |
| 5,681,550 A | 10/1997 | Rubino |
| 5,792,447 A | 8/1998 | Socci et al. |
| 5,807,540 A * | 9/1998 | Junino et al. .......... 424/61 |
| 5,882,636 A | 3/1999 | Mui et al. |
| 6,192,892 B1 * | 2/2001 | Resler .................. 132/200 |
| 6,306,373 B1 * | 10/2001 | Impernate et al. ...... 424/59 |

OTHER PUBLICATIONS

Schlossman, M. "Manicure Preparation" (Feb., 2000) Poucher's Perfumes, Cosmetics and Soaps, Kluwer Academic Publishers, (9$^{th}$ ed., Butler, H.) pp. 329–338.*

Global Cosmetic Industry, Feb. 2001, Advanstar Communications, "Pheonix Chemical" p. 17.*

* cited by examiner

Primary Examiner—Sreeni Padmanabhan
Assistant Examiner—Gina C. Yu
(74) Attorney, Agent, or Firm—Duane Morris LLP

(57) ABSTRACT

A phthalate-free long-lasting nail polish enamel composition consisting of a film-forming agent, solvents, one or more colorants, one or more suspending agents, adhesion promoters, and plasticizers selected from the group consisting of trioctyl trimellitate, butylphthalimide isopropylphthalimide, benzyl benzoate, dioctyl malate, dioctyl sebacate, and mixtures thereof is provided. The nail composition is optionally free of any toluene-containing components, depending upon the desired application.

28 Claims, No Drawings

PHTHALATE FREE NAIL POLISH ENAMEL COMPOSITION EMPLOYING NOVEL PLASTICIZERS

This application claims priority of Provisional Application Ser. No. 60/264,400 which was filed on Jan. 26, 2001.

BACKGROUND OF THE INVENTION

1. Field of Invention

The present invention relates generally to cosmetics and cosmetic formulations for external use on the body; and more particularly to novel long lasting nail polishes, lacquers, and enamels that do not include phthalate-containing compounds.

2. Description of Related Background Art

Cosmetics and their use as decorative applications for the human body have been in existence for centuries and are used extensively throughout the world. As a multibillion-dollar industry, cosmetics have many different applications, including the use of lipstick, eyeliner, facial creams, powders, highlighters, and nail polishes or lacquers. Used primarily by women, the extent of cosmetic use is extraordinary, and has made many of the cosmetics producing and marketing firms very profitable endeavors.

The nail polish sector of the cosmetic industry is extremely competitive. New colors, combinations, including clear formulations and variations thereof are constantly being introduced in an attempt by the formulator to get and hold onto a bigger piece of the market share. The scientific research that is poured into these endeavors is considerable and new products and/or brand names are continually being introduced.

Nail polishes are essentially comprised of pigments and/or dyes that are incorporated and suspended in various solvents and bases. The polishes are also stabilized in the suspension to protect the appearance of the product and to prevent the pigments, during the shelf life of the product, from floating, settling, separating, or striating the polish. Nail polishes are also formulated so that the film formed thereby is tough and durable and adheres to the human nail and will not readily crack, chip, peel, splinter, or become brittle after application and during wear. The toughness should last for an extended period of time, thereby enhancing the durability of the nail polish enamel.

Nail enamels conventionally comprise a film forming component, which typically is nitrocellulose, cellulose acetate butyrate, or a combination of one or both of these cellulosic compounds with a polyurethane or other polymeric compound. Nail enamels have also traditionally included plasticizers, typically a phthalate such as dibutyl phthalate, or camphor, and have also typically included as an adhesion promoter, a polymeric component formed by the condensation polymerization of formaldehyde or other aldehyde, typically an aromatic sulfonamide-aldehyde condensation resin such as o-, p- toluene sulfonamide formaldehyde resin, or a polyester resin such as phthalic anhydride trimellitic anhydride/glycol copolymer.

It has recently become desirable to produce a nail enamel with reduced amounts of phthalate and aldehyde (e.g., formaldehyde) condensation products, in order to alleviate concerns that some wearers may become sensitive to these compounds or susceptible to uncondensed aldehyde in the nail enamel. It is also desirable to reduce the amounts of any volatile components, as the loss of the volatile component through evaporation causes variability in the performance of the nail enamel. Attempts to formulate such nail enamels, however, have encountered difficulties in attaining the desired properties of the nail enamel, such as long wear, high gloss, resistance to chipping on the nail, and compatibility with other nail enamel ingredients. By reducing the amounts of phthalate and aldehydes, for example, the aforementioned properties heretofore have been adversely affected by changes in the ingredients and the amounts thereof in the nail enamel formulation.

Therefore, there is still a need for a nail enamel formulation exhibiting satisfactory properties that contains no phthalate and/or aldehyde condensation products, while exhibiting superior suspension and stability characteristics for long shelf life duration in addition to high gloss, brilliant color and sheen that does not chip or crack during use and will withstand household chemical and varying temperature environments. There also remains a need for the use of the novel plasticizers disclosed herein, to avoid harm to the user's health or to the environment.

U.S. Pat. No. 5,066,484 to Castrogiovanni et al. discloses a number of formulations including glycerol triesters useful as plasticizers in nail polish compositions. The formulations further comprise a film-forming component, a solvent, pigments and other optional compounds. U.S. Pat. No. 5,145,670 to Castrogiovanni et al. discloses nail compositions comprised of glycerol triacetates and trioctanoates as the plasticizers. U.S. Pat. No. 5,225,185 to Castrogiovanni et al. discloses nail lacquers in which the formulation is free of formaldehyde and phthalate, and the plasticizer is comprised of a copolymer formed by the condensation polymerization of formaldehyde and/or other aldehyde, typically an aromatic sulfonamidealdehyde condensation resin. U.S. Pat. No. 5,227,155 to Castrogiovanni et al. discloses nail lacquers with glycerol triacetylricinoleate and glycerol tribenzoate as the plasticizers.

U.S. Pat. No. 5,133,966 to Khamis discloses nail polish formulations comprising improved pigment suspension systems. More specifically, the suspensions comprise carboxylic acids and their salts with a resin carrier in a buffered coating process that is described as yielding a hydrophobic coating with increased dispersion characteristics. U.S. Pat. No. 5,174,996 to Weber et al. discloses nail enamels with improved flotation, migration, and settlement characteristics, which features are achieved by coating pigments with oxidized polyethylene.

U.S. Pat. No. 5,882,636, assigned to the assignee herein, describes phthalate-free nail polish enamel that includes a film-forming agent, solvents, one or more colorants, one or more suspending agents, adhesion promoters, and plasticizers. The plasticizers used include adipates, pentaerythrityl tetrabenzoate, 2,2,4-trimethyl-1,3-pentanediol diisobutyrate, pentaerythrityl tetraacetate, and mixtures thereof.

SUMMARY OF THE INVENTION

Briefly described, a preferred embodiment of the present invention provides a phthalatefree, nail polish enamel composition comprising: a film-forming agent; an organic solvent; a suspending agent; an adhesion promoter selected from the group consisting of: tosylamide epoxy resin, adipic acid/neopental glycol/trimellitic anhydride copolymer, phthalic anhydride/trimellitic anhydride/glycol copolymer, tosylamide formaldehyde resins, and mixtures thereof; and, a plasticizer selected from the group consisting of: trioctyl trimellitate, butylphthalimide isopropylphthalimide, benzyl benzoate, dioctyl malate, dioctyl sebacate, and mixtures thereof. The plasticizer is present in the composition in an amount ranging from about 0.1 to about 15.0 weight percent. A coloring agent may also be added as desired.

The film-forming agent is selected from the group consisting of: nitrocellulose, cellulose acetate butyrate, polyurethanes, acrylics, and mixtures thereof. The solvent is selected from the group consisting of butyl acetate, propyl acetate, ethyl acetate, isopropanol, butyl alcohol, and mixtures thereof. The suspending agent is selected from the group consisting of stearalkonium hectorite, stearalkonium bentonite, montmorillonite clays, treated clays, and mixtures thereof. The coloring agent is selected from the group consisting of D&C and FD&C colorants, inorganic pigments, organic pigments, mica, guanine, and mixtures thereof. Depending upon the application desired, all of the compositions described herein are optionally free of toluene.

In an alternative preferred embodiment, the present invention includes a phthalate-free, nail polish enamel composition comprising: a film-forming agent; an organic solvent; a suspending agent; an adhesion promoter selected from the group consisting of: tosylamide epoxy resin, adipic acid/neopental glycol/trimellitic anhydride copolymer, phthalic anhydride/trimellitic anhydride/glycol copolymer, tosylamide formaldehyde resins, and mixtures thereof; and, butylphthalimide isopropylphthalimide as a plasticizer. Butylphthalimide isopropylphthalimide is present in the composition in an amount ranging from about 3.0 to about 4.0 weight percent.

In a further alternative preferred embodiment, the present invention includes a phthalatefree, nail polish enamel composition comprising: a film-forming agent; an organic solvent; a suspending agent; an adhesion promoter selected from the group consisting of: tosylamide epoxy resin, adipic acid/neopental glycol/trimellitic anhydride copolymer, phthalic anhydride/trimellitic anhydride/glycol copolymer, tosylamide formaldehyde resins, and mixtures thereof; and trioctyl trimellitate, benzyl benzoate, and butylphthalimide isopropylphthalimide as plasticizers. The combined weight percent of said trioctyl trimellitate, benzyl benzoate, and butylphthalimide isopropylphthalimide present in the composition preferably ranges from about 6.0 to about 8.0, and alternatively, are present in the composition as approximately 6.5 weight percent.

DETAILED DESCRIPTION OF THE INVENTION

The improved nail enamels and/or lacquers of the present invention are free of phthalates, and preferably other organic solvents such as toluene, yet exhibit superior shelf life stability, wear life and durability through the incorporation of at least one preferred plasticizer described herein, and preferably, two or more of the plasticizers and adhesion promoters. The present formulations are highly shelf stable and promote a superior film coating on the nail.

Typically, nail polish or enamel formulations include nitrocellulose as the primary film-forming agent, however, the tensile strength and the adhesive qualities of the enamel for the nail surface are generally inferior if nitrocellulose is used without plasticizers. Other known ingredients included in nail enamel formulations, i.e., plasticizers, resins, pigments and thixotropic agents are added as needed, depending upon the particular application to which the nail enamel is intended.

Nail enamels must be durable to resist various physical and harsh household chemical attacks and must also be flexible, as the human nail is pliable and grows with time. To improve the tensile strength and adhesion characteristics of nail enamels, plasticizers and resins have generally been added to the nitrocellulose film forming composition. Dibutyl phthalate has been used as the plasticizer of choice for many years by providing excellent flexibility, elongation and tensile strength to nail polish formulations. There are concerns, however, that dibutyl phthalate may generate toxic side effects to the wearer and may raise environmental concerns at the industry level.

Therefore, it is desirable and also beneficial to replace the present plasticizers typically used in nail polish compositions with those that are free of phthalate and do not raise the same toxic and environmental concerns, are compatible and stable with the other ingredients found in nail polish compositions, and yet still afford the superior durability and flexible necessary for a long lasting nail color and sheen. Accordingly, it has been found that the plasticizers employed in the present invention have not heretofore been used in nail polish formulations, advantageously exhibit improved properties in the resulting formulations over plasticizers previously used, and are a useful alternative plasticizer in formulating nail polishes.

The nail polish compositions of the present invention are free of phthalates. The compositions optionally contain some residual toluene, depending on the formulation characteristics desired. Preferably, the compositions are both phthalate and toluene free, however some fomulations provide superior durability and flexibility with minor amounts of toluene added. Otherwise, the nail polish enamel compositions of the present invention are comprised of conventional ingredients, for example, nitrocellulose as a primary film forming agent, in addition to acrylate copolymers that may be added as a secondary film forming agent; solvents such as isopropyl alcohol, diacetone alcohol, ethyl, butyl, or propyl acetate, and optionally, toluene as a solvent; phthalic anhydride/trimellitic anhydride/glycol copolymers and tosylamide formaldehyde resins, tosylamide epoxy resin, adipic acid/neopental glycol/trimellitic anhydride copolymer as adhesion promoters; and, any one or more of FD&C colorants useful for adding color to the composition.

The plasticizer which gives the superior performance of the enamel of the present invention is selected from the group consisting of: 1) trioctyl trimellitate (tri (2-ethylhexyl) trimellitate); 2) butylphthalimide isopropylphthalimide; 3) benzyl benzoate; 4) dioctyl malate; 5) dioctyl sebacate; and mixtures thereof.

Butylphthalimide isopropylphthalimide is the preferred plasticizer, and is incorporated in the nail enamel formulations of the present invention in amounts of from 0.1 to 15.0 weight percent (wt %) based on the total weight of the enamel composition.

Butylphthalimide isopropylphthalimide is a solution blend of two imides, comprised of N-butylphthalimide and N-isopropylphthalimide, sold under the trade name Pelemol BIP, available from Phoenix Chemical, Inc. in Somerville, N.J., is represented by the chemical structure as follows:

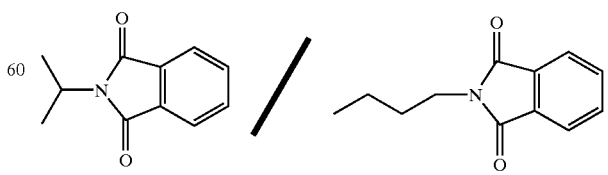

Trioctyl trimellitate (tri(2-ethylhexyl)trimellitate) an ester, is also known under the trade names of TOTM available from Eastman in Kingsport, Tenn., and Pelemol TOTM, available from Phoenix Chemical, Inc. in Somerville, N.J., is represented by the following chemical structure:

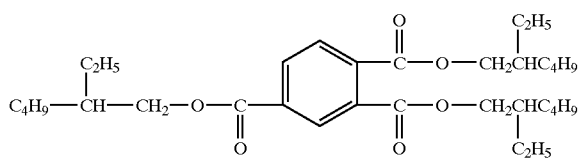

Benzyl benzoate, an ester available under the trade name Moreflex Benzyl Benzoate from Moreflex in Greensboro, N.C., or under the trade name Pelemol B66, available from Phoenix Chemical, Inc. in Somerville, N.J., has the following chemical structure

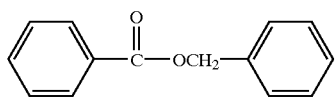

Dioctyl malate, an ester also known as bis(2-ethylhexyl) malate is available under the trade name Dermol DOM from Alzo International Inc. in Sayreville, N.J., and is represented by the chemical structure:

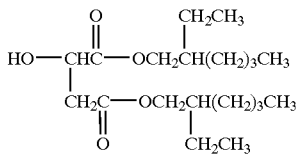

Dioctyl sebacate, an ester also known as di-(2-ethylhexyl) sebacate, is available under the trade name Hallstar DOS from Hall in Bedford Park, Ill., and Jeetox T-5 from Jeen in Fairfield, N.J., has the following chemical structure:

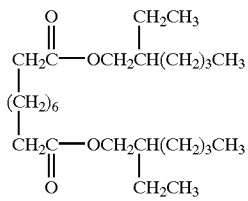

The preferred plasticizer is butylphthalimide isopropylphthalimide. Alternatively, a preferred combination of plasticizers includes butylphthalimide isopropylphthalimide, benzyl benzoate, and trioctyl trimellitate. The novel plasticizers are incorporated in the nail enamel formulations of the present invention ranging in the amounts of about 0.1–15.0 wt %.

The remaining ingredients in the novel nail enamel formulations of the present invention include those compounds well known in the nail polish industry. A film forming agent is necessary in order to provide the nail enamel with a consistency that results in the formulation of a uniform, stable film on the surface of the nail when the enamel is applied thereon. Nitrocellulose is the preferred film former and must be incorporated in the formulation in amounts that will cause the enamel to readily spread out about the surface of the nail yet remain viscous enough to not run or drip therefrom. However, it must also readily cling to and flow from the applicator brush as the enamel is applied from bottle to nail and this generally comprises from about 5.0 to 40 wt % of the total weight of the composition and preferably will be incorporated in amounts of from about 3 to about 30 wt %. Other suitable film formers include cellulose acetate butyrate, polyurethanes, and mixtures thereof.

The solvent components are selected to be as inert as possible to the user's nail, and to other components of the nail enamel composition. The solvent should also be capable of dissolving or dispersing the other components so that they readily flow onto the nail. The solvent must be able to evaporate from the nail in a matter of minutes at room temperature and pressure so that the film forming agents, plasticizers and other components dissolved therein solidify and adhere to the nail surface. Examples of preferred solvents include isopropanol, butyl acetate, ethyl acetate, propyl acetate, and mixtures thereof. Effective amounts of the solvent component will generally lie in the range of about 30 wt % to about 70 wt % of the composition.

A suspending agent is an optional and preferred component of the nail enamel compositions of the present invention. The suspending agent should suspend the pigments in the nail enamel, and adjust the viscosity thereof to achieve desired flowability. Examples of preferred suspending agents include montmorillonite clays, and treated clays such as stearalkonium hectorite and bentonite. The amount of the suspending agent of course depends on the desired flow characteristics of the nail enamel. Amounts ranging from about 0.2 to about 2.0 wt % are generally satisfactory.

The nail enamel compositions of the present invention can be clear, i.e., unpigmented, or they can include a pigment component. Suitable pigments include the inorganic and organic pigments that are useable in cosmetic formulations. For example, particular examples of suitable pigments include titanium dioxide, D&C Red #6 Barium Lake, D&C Red #7 Calcium Lake, D&C Red #34 Calcium Lake, FD&C Yellow #5 Aluminum Lake, Ferric Ferrocyanide, Red Iron oxide, Black Iron Oxide, Mica, Bismuth Oxychloride, Guanine, D&C Red #17, D&C Red #33, D&C Violet #2, D&C Yellow #11, FD&C Blue #1 and FD&C Green #3.

The term "pigment" includes mixtures of one or more of the foregoing compounds. These pigments can be surface treated for improved performance. See U.S. Pat. No. 5,133,966 to Khamis; U.S. Pat. No. 4,832,944 to Socci et al. and U.S. Pat. No. 5,174,996 to Weber et al., the disclosures of all of which are hereby incorporated herein by reference.

The amounts of any particular ingredients comprising the pigment component will of course depend on the shade desired by the practitioner. In general, the pigment component comprises about 0.01 to about 15.0 wt % of the composition.

Nail enamel compositions in accordance with the present invention can be manufactured by thoroughly and intimately mixing together all the components indicated above, in the amounts described above. Examples of satisfactory equipment and how to use it are readily apparent to one of ordinary skill in the art.

The mixing procedure for the nail enamel formulations of the present invention is as those generally known in the art wherein the film-forming component is first mixed into the solvent, followed by the plasticizer, and thereafter the remaining ingredients. All components are added while mixing.

The nail enamel formulation of the present invention, as stated before, provides a superior long-lasting color and gloss that is chip resistant, durable, flexible and will withstand harsh household chemicals, adverse temperatures and the effects of other external factors for long periods of time.

The following examples are provided to more specifically define the formulations of the present invention and to disclose preferred embodiments of the nail enamels. They are presented for illustrative purposes only and it is recognized that there are minor changes and alterations that can be made with respect to the ingredients and/or their amounts not disclosed herein. It should be understood that to the extent any such changes do not materially affect the final composition or its functionality, they are considered to fall within the spirit and scope of the invention as later recited in the claims. In all of the following Examples, the values provided represent weight percentages based on 100% of the total weight of the composition.

EXAMPLE 1

Time Release Nail Enamel

| | |
|---|---|
| Ethyl Acetate | 18.368 wt % |
| Butyl Acetate | 3.772 wt % |
| Isopropyl Alcohol | 2.979 wt % |
| Butyl Alcohol | 1.490 wt % |
| Nitrocellulose solution in Isopropyl Alcohol/Ester Solvents | 27.462 wt % |
| Polyester Resin | 6.951 wt % |
| Tosyamide/Epoxy Resin | 4.964 wt % |
| Acrylates Copolymer | 2.483 wt % |
| Stearalkonium Hectorite/Bentonite Gel | 13.901 wt % |
| Fumed Silica Gel | 9.430 wt % |
| Dioctyl Adipate | 1.500 wt % |
| Benzyl Benzoate | 1.000 wt % |
| Butylphthalimide Isopropylphthalimide | 3.000 wt % |
| Trioctyl Trimellitate | 2.500 wt % |
| UV Absorber | 0.200 wt % |
| TOTAL | 100.00 wt % |

A nail polish enamel was prepared using the above-identified ingredients. This formulation incorporates a combination of three novel plasticizers, i.e., benzyl benzoate, butylphthalimide isopropylphthalimide, and trioctyl trimellitate which provide a time-release nail enamel, in addition to an adipate.

The sample was tested for hardness as is known in the art, and compared to the hardness of a conventional phthalate-containing nail enamel. The samples were drawn on a 4"×7" glass plate at a thickness of about 6 millimeters, allowed to dry, and then subjected to the Persoz Hardness test at various time intervals as indicated below. The number of pendulum swings was recorded as shown.

| Time Interval (in hours) | 16 | 24 | 48 | 72 | 96 |
|---|---|---|---|---|---|
| Hardness (Example 1) | 85 | 98 | 125 | 130 | 143 |
| Hardness (phthalate enamel) | 80 | 105 | 138 | 176 | 230 |

After 72 hours, the film performance of the formula of Example 1 still exhibits good adhesion and flexibility, while the nail enamel containing phthalate is brittle.

Adhesion was tested using a Cross Cut Tester, ASTM D3002, ASTM D3359, where the film thickness is approximately 6 millimeters. The cross-cut test is a simple and easy test method for evaluating the adhesion of single or multi-coat systems. The Cross-Cut test involves cutting a lattice pattern through the film to the substrate with an appropriate tool. The film is then brushed lightly with a soft brush to remove any detached flakes or ribbons of coating. The grid area is thereafter inspected using an illuminated magnifier to determine the extent of removal of the coating from the substrate and is rated according to a predetermined scale.

| Time Interval (in hours) | 24 | 72 |
|---|---|---|
| Adhesion (Example 1) | Gt 0/5 B | Gt 1/4 B–Gt 0/5 B |
| Adhesion (phthalate enamel) | Gt 1/4 B | Gt 3/2 B |

Based on the results of the Cross Cut test, after 24 hours the formula of Example 1 exhibits smooth edges of the cuts, and none of the squares of the lattice is detached, whereas the phthalate containing enamel has small flakes of coating detached at the intersections of the cuts, affecting less than 5% of the area affected. Even after 72 hours, the formula of Example 1 has only small flakes of coating detached, whereas the coating of the phthalate containing enamel is flaked along the edges and/or parts of the squares, and the area affected is 15 to 35% of the lattice.

EXAMPLE 2

Long Wearing Nail Enamel

| | |
|---|---|
| Ethyl Acetate | 23.247 wt % |
| Butyl Acetate | 22.307 wt % |
| Nitrocellulose 70% in Isopropyl Alcohol | 14.710 wt % |
| Polyester Resin | 11.200 wt % |
| Dioctyl Adipate | 4.605 wt % |
| Butylphthalimide Isopropylphthalimide | 3.733 wt % |
| Sucrose Benzoate | 2.831 wt % |
| Adhesion Promoter Resin | 2.831 wt % |
| UV Absorber | 0.149 wt % |
| Citric Acid Solution | 0.200 wt % |
| Stearalkonium Hectorite/Bentonite Gel | 14.187 wt % |
| TOTAL | 100.00 wt % |

A nail polish composition was prepared using the above-identified ingredients. The sole novel plasticizer used was butylphthalimide isopropylphthalimide, in combination with dioctyl adipate, which provides a long wearing nail enamel.

The sample was tested for hardness as in Example 1. The number of pendulum swings was recorded as shown below.

| Time Interval (in hours) | 24 | 48 | 72 | 96 |
|---|---|---|---|---|
| Hardness (Example 2) | 88 | 130 | 132 | 139 |
| Hardness (phthalate enamel) | 80 | 138 | 176 | 230 |

As with Example 1, the film performance of the formula of Example 2 at 72 hours exhibits good adhesion and flexibility. The phthalate enamel, however, is brittle at 72 hours.

The adhesion of the samples was also tested using a Cross-Cut tester as in Example 1. The results of the test are shown below.

| Time Interval (in hours) | 24 | 72 |
|---|---|---|
| Adhesion (Example 2) | Gt 0/5 B | Gt 1/4 B–Gt 0/5 B |
| Adhesion (phthalate enamel) | Gt 1/4 B | Gt 3/2 B |

Based on the results of the Cross-Cut test, after 24 hours, the formula of Example 2 exhibits smooth edges, and none of the squares are detached, whereas the formula containing phthalate has small flakes of coating detached. At 72 hours, the formula of Example 2 has only small flakes of coating detached, but the phthalate containing formula is flaked along the edges and/or parts of the squares and the area affected is 15 to 35% of the lattice.

EXAMPLE 3

Acrylic Nail Enamel

| | |
|---|---|
| Ethyl Acetate | 33.400 wt % |
| PM Acetate | 3.000 wt % |
| Nitrocellulose 70% in Isopropyl Alcohol | 5.000 wt % |
| Acrylates Copolymer | 25.000 wt % |
| Acrylates/Dimethicone Copolymer | 3.000 wt % |
| Dioctyl Adipate | 3.000 wt % |
| Butylphthalimide Isopropylphthalimide | 3.600 wt % |
| Polyester Resin | 5.600 wt % |
| UV Absorber | 0.200 wt % |
| Citric Acid Solution | 0.200 wt % |
| Stearalkonium Hectorite/Bentonite Gel | 18.000 wt % |
| TOTAL | 100.00 wt % |

A nail polish composition was prepared using the above-identified ingredients. In this Example, butylphthalimide isopropylphthalimide is used as a plasticizer, in conjunction with dioctyl adipate and acrylates to provide an acrylic nail enamel.

The sample was tested for hardness as in Example 1. The number of pendulum swings was recorded as shown below.

| Time Interval (in hours) | 24 | 48 | 72 | 96 |
|---|---|---|---|---|
| Hardness (Example 3) | 100 | 140 | 145 | 148 |
| Hardness (phthalate enamel) | 105 | 138 | 176 | 230 |

As with Example 1, the film performance of the formula of Example 3 at 72 hours exhibits good adhesion and flexibility. The phthalate enamel, however, is brittle at 72 hours.

The adhesion of the samples was also tested using a Cross-Cut tester as in Example 1. The results of the test are shown below.

| Time Interval (in hours) | 24 | 72 |
|---|---|---|
| Adhesion (Example 3) | Gt 0/5 B | Gt 1/4 B–Gt 0/5 B |
| Adhesion (phthalate enamel) | Gt 2/3 B–Gt 1/4 B | Gt 3/2 B |

Based on the results of the test, the formula of Example 3 exhibits similar properties to that of Examples 1 and 2.

EXAMPLE 4

Long Lasting Nail Enamel

| | |
|---|---|
| Ethyl Acetate | 18.368 wt % |
| Butyl Acetate | 3.772 wt % |
| Isopropyl Alcohol | 2.979 wt % |
| Butyl Alcohol | 1.490 wt % |
| Nitrocellulose solution in Isopropyl Alcohol/Ester Solvents | 27.462 wt % |
| Polyester Resin | 6.951 wt % |
| Tosyamide/Epoxy Resin | 4.964 wt % |
| Acrylates Copolymer | 2.483 wt % |

EXAMPLE 4-continued

Long Lasting Nail Enamel

| | |
|---|---|
| Stearalkonium Hectorite/Bentonite Gel | 13.901 wt % |
| Fumed Silica Gel | 9.430 wt % |
| Benzyl Benzoate | 2.500 wt % |
| Butylphthalimide Isopropylphthalimide | 3.000 wt % |
| Trioctyl Trimellitate | 2.500 wt % |
| UV Absorber | 0.200 wt % |
| TOTAL | 100.00 wt % |

A nail polish composition was prepared using the above-identified components. This composition includes a combination of benzyl benzoate, butylphthalimide isopropylphthalimide, and trioctyl trimellitate as plasticizers, in the absence of an adipate to provide a long lasting nail enamel.

The sample was tested for hardness as in Example 1. The number of pendulum swings was recorded as shown below.

| Time Interval (in hours) | 24 | 48 | 72 | 96 |
|---|---|---|---|---|
| Hardness (Example 3) | 90 | 130 | 133 | 136 |
| Hardness (phthalate enamel) | 80 | 138 | 176 | 230 |

The adhesion of the samples was also tested using a Cross-Cut tester as in Example 1. The results of the test are shown below.

| Time Interval (in hours) | 24 | 72 |
|---|---|---|
| Adhesion (Example 3) | Gt 0/5 B | Gt 1/4 B-Gt 0/5 B |
| Adhesion (phthalate enamel) | Gt 1/4 B | Gt 3/2 B |

As indicated by the data, the preferred plasticizer, butylphthalimide isopropylphthalimide shows superior results. Alternatively, a combination of plasticizers, namely, benzyl benzoate, butylphthalimide isopropylphthalimide, and trioctyl trimellitate, also provide superior results.

What is claimed is:

1. A phthalate-free, nail polish enamel composition comprising: a film-forming agent; an organic solvent; a suspending agent; an adhesion promoter selected from the group consisting of: tosylamide epoxy resin, adipic acid/neopental glycol/trimellitic anhydride copolymer, phthalic anhydride/trimellitic anhydride/glycol copolymer, tosylamide formaldehyde resins, and mixtures thereof; and a plasticizer selected from the group consisting of: (a) butylphthalimide is isopropylphthalimide, and (b) a mixture of butylphthalimide isopropylphthalimide with at least one of benzyl benzoate, dioctyl malate, dioctyl sebacate and trioctyl trimellitate.

2. The composition of claim 1, wherein said plasticizer is present in the composition in an amount ranging from about 0.1 to about 15.0 weight percent.

3. The composition of claim 2, wherein said film-forming agent is selected from the group consisting of: nitrocellulose, cellulose acetate butyrate, polyurethanes, acrylics, and mixtures thereof.

4. The composition of claim 2, wherein said solvent is selected from the group consisting of butyl acetate, propyl acetate, ethyl acetate, isopropanol, butyl alcohol, and mixtures thereof.

5. The composition of claim 2, wherein said suspending agent is selected from the group consisting of stearalkonium hectorite, stearalkonium bentonite, montmorillonite clays, treated clays, and mixtures thereof.

6. The composition of claim 2, wherein said composition further comprises a coloring agent selected from the group consisting of D&C colorants, FD&C colorants, inorganic pigments, organic pigments, mica, guanine, and mixtures thereof.

7. A phthalate-free, nail polish enamel composition comprising: a film-forming agent; an organic solvent; a suspending agent; an adhesion promoter selected from the group consisting of: tosylamide epoxy resin, adipic acid/neopental glycol/trimellitic anhydride copolymer, phthalic anhydride/trimellitic anhydride/glycol copolymer, tosylamide formaldehyde resins, and mixtures thereof; and, butylphthalimide isopropylphthalimide as a plasticizer.

8. The composition of claim 7, wherein butylphthalimide isopropylphthalimide is present in the composition in an amount ranging from about 3.0 to about 4.0 weight percent.

9. The composition of claim 8, wherein said film-forming agent is selected from the group consisting of: nitrocellulose, cellulose acetate butyrate, polyurethanes, acrylics, and mixtures thereof.

10. The composition of claim 9, wherein said solvent is selected from the group consisting of butyl acetate, propyl acetate, ethyl acetate, isopropanol, butyl alcohol, and mixtures thereof.

11. The composition of claim 10, wherein said suspending agent is selected from the group consisting of stearalkonium hectorite, stearalkonium bentonite, montmorillonite clays, treated clays, and mixtures thereof.

12. The composition of claim 11, further comprising a coloring agent selected from the group consisting of D&C colorants, FD&C colorants, inorganic pigments, organic pigments, mica, guanine, and mixtures thereof.

13. A phthalate-free, nail polish enamel composition comprising: a film-forming agent; an organic solvent; a suspending agent; an adhesion promoter selected from the group consisting of: tosylamide epoxy resin, adipic acid/neopental glycol/trimellitic anhydride copolymer, phthalic anhydride/trimellitic anhydride/glycol copolymer, tosylamide formaldehyde resins, and mixtures thereof; and trioctyl trimellitate, benzyl benzoate, and butylphthalimide isopropylphthalimide as plasticizers.

14. The composition of claim 13, wherein said combined weight of said plasticizers are present in the composition in an amount ranging from about 0.1 to about 15.0 weight percent.

15. The composition of claim 13, wherein the combined weight percent of said trioctyl trimellitate, benzyl benzoate, and butylphthalimide isopropylphthalimide present in the composition ranges from about 6.0 to about 8.0 wt %.

16. The composition of claim 13, wherein the combined weight percent of said trioctyl trimellitate, benzyl benzoate, and butylphthalimide isopropylphthalimide present in the composition is approximately 6.5 weight percent.

17. The composition of claim 14, wherein said solvent is selected from the group consisting of butyl acetate, propyl acetate, ethyl acetate, isopropanol, butyl alcohol, and mixtures thereof.

18. The composition of claim 17, wherein said film-forming agent is selected from the group consisting of: nitrocellulose, cellulose acetate butyrate, polyurethanes, acrylics, and mixtures thereof.

19. The composition of claim 18, wherein said suspending agent is selected from the group consisting of stearalkonium hectorite, stearalkonium bentonite, montmorillonite clays, treated clays and mixtures thereof.

20. The composition of claim 14, wherein said composition is toluene-free.

21. The composition of claim 14, further comprising a coloring agent selected from the group consisting of: D&C colorants, FD&C colorants, inorganic pigments, organic pigments, mica, guanine, and mixtures thereof.

22. A plasticizer for use in a phthalate-free nail polish composition, comprising a mixture of trioctyl trimellitate, butylphthalimide isopropylphthalimide, and benzyl benzoate.

23. A method for making a phthalate-free nail enamel composition comprising: providing a film-forming component; mixing said film-forming component with one or more solvents; and adding to said film-forming component and solvent a plasticizer selected from the group consisting of: (a) butylphthalimide isopropylphthalimide, and (b) a mixture of butylphthalimide isopropylphthalimide with at least one of benzyl benzoate, dioctyl malate, dioctyl sebacate and trioctyl trimellitate.

24. The method of claim 23 wherein said plasticizer is present in the composition in an amount ranging from about 0.1 to about 15.0 weight percent.

25. The method of claim 23, wherein said film-forming agent is selected from the group consisting of: nitrocellulose, cellulose acetate butyrate, polyurethanes, acrylics, and mixtures thereof.

26. The method of claim 23, wherein said solvent is selected from the group consisting of butyl acetate, propyl acetate, ethyl acetate, isopropanol, butyl alcohol, and mixtures thereof.

27. The method of claim 23, further comprising adding to said film-forming component, solvent, and plasticizer a suspending agent.

28. The method of claim 27, wherein said suspending agent is selected from the group consisting of stearalkonium hectorite, stearalkonium bentonite, montmorillonite clays, treated clays, and mixtures thereof.

* * * * *